(12) United States Patent
Bon Betemps et al.

(10) Patent No.: US 9,175,097 B2
(45) Date of Patent: Nov. 3, 2015

(54) PROCESS FOR THE SIMULTANEOUS SUBSTITUTION AND CROSSLINKING OF A POLYSACCHARIDE VIA ITS HYDROXYL FUNCTIONAL GROUPS

(71) Applicant: LABORATOIRES VIVACY, La Ravoire (FR)

(72) Inventors: Jeremie Bon Betemps, Albens (FR); Estelle Piron, Saint Etienne de Cuines (FR)

(73) Assignee: LABORATOIRES VIVACY, Archamps (FR)

( * ) Notice: Subject to any disclaimer, the term of this patent is extended or adjusted under 35 U.S.C. 154(b) by 144 days.

(21) Appl. No.: 13/692,511

(22) Filed: Dec. 3, 2012

(65) Prior Publication Data

US 2013/0172288 A1  Jul. 4, 2013

Related U.S. Application Data

(60) Provisional application No. 61/566,258, filed on Dec. 2, 2011.

(30) Foreign Application Priority Data

Dec. 2, 2011  (FR) ...................................... 11 61125

(51) Int. Cl.
| | | |
|---|---|---|
| *C08B 15/00* | (2006.01) | |
| *C08B 37/08* | (2006.01) | |
| *C08B 37/00* | (2006.01) | |
| *C08L 1/28* | (2006.01) | |
| *C08L 5/00* | (2006.01) | |
| *C08L 5/08* | (2006.01) | |
| *C07H 15/12* | (2006.01) | |
| *A61K 31/715* | (2006.01) | |
| *A61K 8/73* | (2006.01) | |
| *A61Q 19/08* | (2006.01) | |
| *A61K 31/717* | (2006.01) | |
| *A61K 31/722* | (2006.01) | |
| *A61K 31/728* | (2006.01) | |
| *A61K 31/738* | (2006.01) | |
| *A61K 9/00* | (2006.01) | |
| *A61K 47/36* | (2006.01) | |

(52) U.S. Cl.
CPC .............. *C08B 37/0006* (2013.01); *A61K 8/735* (2013.01); *A61K 31/715* (2013.01); *A61K 31/717* (2013.01); *A61K 31/722* (2013.01); *A61K 31/728* (2013.01); *A61K 31/738* (2013.01); *A61Q 19/08* (2013.01); *C07H 15/12* (2013.01); *C08B 15/005* (2013.01); *C08B 37/00* (2013.01); *C08B 37/003* (2013.01); *C08B 37/0072* (2013.01); *C08L 1/286* (2013.01); *C08L 5/00* (2013.01); *C08L 5/08* (2013.01); *A61K 9/0019* (2013.01); *A61K 47/36* (2013.01); *A61K 2800/91* (2013.01)

(58) Field of Classification Search
None
See application file for complete search history.

(56) References Cited

U.S. PATENT DOCUMENTS

| 3,046,272 | A | 7/1962 | Strating et al. |
|---|---|---|---|
| 4,175,183 | A | 11/1979 | Ayers |
| 4,321,367 | A | 3/1982 | Cheng et al. |
| 4,582,865 | A | 4/1986 | Balazs et al. |
| 4,605,691 | A | 8/1986 | Balazs et al. |
| 4,713,448 | A | 12/1987 | Balazs et al. |
| 4,716,154 | A | 12/1987 | Malson et al. |
| 4,716,224 | A | 12/1987 | Sakurai et al. |
| 4,772,419 | A | 9/1988 | Malson et al. |
| 4,863,907 | A | 9/1989 | Sakurai et al. |
| 4,957,744 | A | 9/1990 | della Valle et al. |
| 4,990,609 | A | 2/1991 | Herzog et al. |
| 5,128,326 | A | 7/1992 | Balazs et al. |
| 2006/0246137 | A1 | 11/2006 | Hermitte et al. |

FOREIGN PATENT DOCUMENTS

| CN | 1590444 A | 3/2005 |
|---|---|---|
| EP | 0 265 116 A2 | 4/1988 |
| EP | 0 341 745 A1 | 11/1989 |
| EP | 0 507 604 A2 | 10/1992 |
| EP | 0 749 982 A1 | 12/1996 |

(Continued)

OTHER PUBLICATIONS

Simkovic et al., "Preparation of water-soluble/insoluble derivatives of hyaluronic acid by cross-linking with epichlorohydrin in aqueous NaOH/NH$_4$OH solution," Carbohydrate Polymers, 2000, vol. 41, pp. 9-14.

(Continued)

*Primary Examiner* — Layla Bland
(74) *Attorney, Agent, or Firm* — Oliff PLC

(57) ABSTRACT

A process for the simultaneous substitution and crosslinking of a polysaccharide via its hydroxyl functional groups, in an aqueous phase, which includes the following steps:
  a polysaccharide is placed in an aqueous medium,
  it is brought into the presence of at least one precursor of a substituent,
  it is brought into the presence of a crosslinking agent,
  the substituted and crosslinked polysaccharide is obtained and isolated,
wherein process is carried out in the presence of a basic or acidic catalyst, the concentration of which is between $3.16 \times 10^{-7}$ and 0.32 mol/L, and at a temperature of less than 60° C. In one embodiment, the polysaccharide is in the form of a gel or hydrogel which is used in particular as augmentation biomaterial.

30 Claims, 2 Drawing Sheets

(56) References Cited

FOREIGN PATENT DOCUMENTS

| EP | 1 942 117 A1 | 7/2008 |
|---|---|---|
| WO | WO 99/43728 | 9/1999 |
| WO | WO 2005/012364 A2 | 2/2005 |
| WO | WO 2011/148116 A2 | 12/2011 |

OTHER PUBLICATIONS

Rocha De Souza et al., "Antioxidant activities of sulfated polysaccharides from brown and red seaweeds," J Appl Phycol., Apr. 2007, vol. 19(2), pp. 153-160.

Jul. 23, 2012 Search Report issued in French Application No. 1161125 (with translation).

Aug. 4, 2015 Notification of the First Office Action issued in Chinese Application No. 201280064284.X.

PROCESS FOR THE SIMULTANEOUS SUBSTITUTION AND CROSSLINKING OF A POLYSACCHARIDE VIA ITS HYDROXYL FUNCTIONAL GROUPS

BACKGROUND OF THE INVENTION

The present invention relates to novel crosslinked and substituted biocompatible polysaccharides, characterized by improved rheological properties and optionally exhibiting advantageous properties introduced by the substituents, such as, for example, a moisturizing or lipophilizing action, in comparison with a conventional crosslinked polysaccharide, and which can be used as biomaterials, in particular in the field of filler surgery, tissue repair or as articular material or fluids.

Numerous substituted and crosslinked polysaccharides are known from the prior art but none of the processes of the prior art has made it possible to obtain polysaccharides exhibiting the synergistically improved rheological properties according to the present invention.

EP 0 265 116 on behalf of FIDIA, describes crosslinked compounds substituted via ester functional groups on the —COOH functional groups of the polysaccharide. Specifically, the hyaluronic acid chains are crosslinked via ester bridges formed by intra- or intermolecular reaction between aliphatic polyalcohols and the carboxylic acid functional groups of the polysaccharide. Substitution also takes place via the ester functional groups of the polysaccharide by the grafting of small molecules carrying hydroxyl functional groups, such as ethanol or benzyl alcohol, for example.

In EP 0 341 745, also on behalf of FIDIA, the polymer is "self-crosslinked" in the sense that the ester functional groups are formed between the carboxyl functional groups of the polysaccharide and the hydroxyl functional groups of one and the same chain or of another chain, without crosslinking agent. The patent also discloses crosslinked and substituted polymers. The substituents are in this instance also alcohol chains, such as ethanol or benzyl alcohol, and are grafted to the polysaccharide via the carboxyl functional groups of the latter.

Patent application WO 99/43728, on behalf of FIDIA, reports hyaluronic acids sulfated in the N-position or O-position. These polysaccharides, which can, as in the above-mentioned patent applications, be self-crosslinked or crosslinked via ester bridges (EP 0 256 116 and EP 0 341 745), are subsequently grafted with polyurethanes. A complex matrix of different cocrosslinked polymers is thus obtained. However, these products are also crosslinked via ester functional groups and furthermore require the use of at least three steps of synthesis in the case of a matrix of O- or N-sulfated polysaccharide and of polyurethane. Thus, they do not present a satisfactory solution.

Patent EP 0 749 982, on behalf of HERCULES, teaches the preparation of polymers substituted by hindered phenol compounds, with antioxidizing properties, which can optionally be crosslinked. The crosslinking is carried out by conventional means of the prior art using polyfunctional epoxides or corresponding halohydrins (U.S. Pat. No. 4,716,224, U.S. Pat. No. 4,863,907, EP 0 507 604 A2, U.S. Pat. No. 4,716,154, U.S. Pat. No. 4,772,419, U.S. Pat. No. 4,957,744), polyhydric alcohols (U.S. Pat. No. 4,582,865, U.S. Pat. No. 4,605,691), divinyl sulfone (U.S. Pat. No. 5,128,326, U.S. Pat. No. 4,582,865) and aldehydes (U.S. Pat. No. 4,713,448). According to the preferred embodiment, the polymer is crosslinked by reaction with carboxylic acids or polyacid anhydrides, in order to again result in the formation of esters. The compounds described in the prior art thus have a high density of ester functional groups in the majority of cases.

Cocrosslinked polymers are also known from the prior art, for example those described in patent application WO 2005/012364, on behalf of ANTEIS, which exhibit an improved persistence by the formation of a matrix by cocrosslinking of one or more polymers. These cocrosslinked polysaccharides can in addition be substituted by polymers having a low average molecular weight or small nonpolymeric molecules. These polymers are generally hyaluronic acid cocrosslinked with cellulose, to which compound will subsequently be grafted, via the crosslinking agent, with small polymers, such as heparin or hyaluronic acid, carrying benzyl esters (Mw<50 000 kDa). In some cases, antioxidants, such as vitamin C, are also grafted via the crosslinking agent.

U.S. Pat. No. 4,605,691, on behalf of Balazs (Biomatrix), also teaches a cocrosslinking process (a process of formation of cocrosslinked polymers). This time it concerns the cocrosslinking of hyaluronic acid with collagen, cellulose, heparin or carminic acid.

The common feature of the processes described in the prior art is that the substitutions or graftings which result in the functionalization take place via the crosslinking agent. In comparison with a crosslinking alone, this is reflected in a competition between reaction for crosslinking and functionalization via the crosslinking agent.

A person skilled in the art should thus always take care to properly adjust the amount of crosslinking agent introduced in order for the functionalization not to limit the crosslinking, which would result in a modification to the final properties of the gel according to the respective kinetics of the reactions.

Specifically, if the crosslinking takes place before the introduction of the functional agent, care will have to be taken, on the one hand, that the functional agent is introduced homogeneously into the crosslinked polymer network and, on the other hand, that there remains sufficient crosslinking agent to functionalize the polymer. If all is consumed, it is then necessary to add a further amount of crosslinking agent; the risk then arises of possible overcrosslinking. In some cases, a person skilled in the art will even have to substitute before crosslinking in order to limit the "competition" effects.

A person skilled in the art will thus still be confronted with a choice: to substitute before or after having crosslinked the polymer and to adjust the reaction conditions, taking into account the polymer/crosslinking agent and functionalization agent/crosslinking agent reaction rates. This choice thus becomes a crucial and problematic step of the process.

Water-soluble celluloses, such as sulfoalkylcelluloses substituted by sulfoalkyls and ethers, are also known. The desired aim is to obtain high functionalization in order to obtain water-soluble sulfoalkylcelluloses; see, for example, U.S. Pat. No. 4,990,609 on behalf of WOLFF WALSRODE. For this type of functionalization, sultones are often used for their high reactivity, which makes possible a high degree of functionalization and improves the solubility of the final product due to the strong presence of sulfonate functional groups. However, if it is desired to crosslink in a second step, the high degrees of substitution can interfere with the satisfactory crosslinking of the polymer. Furthermore, the functionalization conditions are often too drastic for the polysaccharide not to be damaged to the point of irredeemably diminishing its rheological properties; see, for example, the compounds described in U.S. Pat. No. 3,046,272.

This is because it is known that polysaccharides, for example hyaluronic acid, exhibit relatively poor resistance to alkaline conditions and it is known that, during the crosslinking or deacetylation of hyaluronic acid in sodium hydroxide solution, decomposition occurs (Simkovic et al., *Carbohydrate Polymers*, 41, 2000, 9-14); in point of fact, the reactions described in the prior art are often lengthy and/or under pH conditions which result in decomposition.

Under the highly concentrated alkaline conditions and at the high temperatures to which polysaccharides are subjected in processes, such as those described in U.S. Pat. No. 4,321,367 or in U.S. Pat. No. 4,175,183, it has been demonstrated (see the comparative examples below) that decomposition of the polysaccharide takes place.

Thus, in the processes described in the prior art, although relatively easy to carry out, the processes for producing a crosslinked and substituted polymer are very often lengthy and require several steps because of the successive addition of the various ingredients in order to avoid competition between the various polymers and grafts which will be attached to the polysaccharide via the crosslinking agent. Furthermore, due to the reaction times and the reaction conditions, the resulting polymer can have damaged rheological properties.

The present invention makes it possible to solve all of the disadvantages of the processes of the prior art and makes it possible in addition to obtain polysaccharides having rheological properties which are synergistically improved.

It relates to a process for the preparation of crosslinked and substituted polysaccharides. Principally, the crosslinking and substitution reactions in this process are carried out simultaneously, under the same experimental conditions and on the same reaction sites, the hydroxyl functional groups of the polysaccharide, this being the case without there being competition between the different entities involved, the substitutions not being carried out via the crosslinking agent. The degrees of substitution and crosslinking obtained are thus comparable to those obtained by reactions carried out sequentially and the rheological properties of the polysaccharides are improved.

The present invention also relates to a crosslinked and substituted polysaccharide obtained by the process according to the invention, the rheology of which, in particular the viscoelasticity of which, is increased in comparison not only with the simply substituted polysaccharide but also in comparison with the solely crosslinked polysaccharide and in comparison with the substituted and then crosslinked polysaccharide.

In addition, the substituents can introduce advantageous properties, for example biological properties, into the polysaccharide according to the invention, the rheological properties of which are improved. The synergistic effect is all the more surprising as it is retained during the sterilization of the substituted and crosslinked polysaccharide.

The present invention thus makes it possible to combine the advantages relating to the substitution and those relating to the crosslinking without modifying the individual characteristics of each of these modifications taken separately and in particular without damaging the rheological properties since they are synergistically improved.

The invention relates to a process for the simultaneous substitution and crosslinking of a polysaccharide via its hydroxyl functional groups, in an aqueous phase, comprising the following steps:
  a polysaccharide is placed in an aqueous medium,
  it is brought into the presence of at least one precursor of a substituent,
  it is brought into the presence of a crosslinking agent,
  the substituted and crosslinked polysaccharide is obtained and isolated, wherein, said process is carried out in the presence of a basic or acidic catalyst, the concentration of which is between $3.16 \times 10^{-7}$ and 0.32 mol/L, and at a temperature of less than 60° C.

The term "via its hydroxyl functional groups" is understood to mean the fact that the substitutions and the crosslinkings are carried out on the —OH groups carried by the polysaccharides.

The process can also be characterized by a reactive catalyst ratio or RCR.

This reactive catalyst ratio (RCR) is defined as being:

$$RCR = \frac{\text{(Number of moles reactive functional groups of the catalyst introduced into the reaction medium)}}{\text{(Number of moles } disacharide \text{ unit introduced into the reaction medium)}}$$

In one embodiment, the reactive catalyst ratio in the process according to the invention is between 0.02:1 and 3:1.

In one embodiment, the reactive catalyst ratio in the process according to the invention is between 0.2:1 and 3:1.

In one embodiment, the reactive catalyst ratio in the process according to the invention is between 0.3:1 and 3:1.

In one embodiment, the reactive catalyst ratio in the process according to the invention is between 0.5:1 and 2:1.

In one embodiment, the reactive catalyst ratio in the process according to the invention is between 0.7:1 and 1.5:1.

In one embodiment, the reactive catalyst ratio in the process according to the invention is 1.75:1.

In one embodiment, the reactive catalyst ratio in the process according to the invention is 1:1.

In one embodiment, the reactive catalyst ratio in the process according to the invention is 0.8:1.

In one embodiment, the reactive catalyst ratio in the process according to the invention is 0.06:1.

In one embodiment, the catalyst in the process according to the invention is a base.

In this embodiment, the reactive functional group of the catalyst is the HO⁻ ion.

In the aqueous phase, the situation is that pH=14+log ([HO⁻]) and $[HO^-]=10^{-(14-pH)}$.

In one embodiment, the concentration of catalyst HO⁻ in the process according to the invention is between $10^{-6}$ mol/L and 0.32 mol/L, such that $10^{-6}$ mol/L≤[HO⁻]≤0.32 mol/L.

In one embodiment, the concentration of catalyst HO⁻ in the process according to the invention is between $3.16 \times 10^{-4}$ mol/L and $3.16 \times 10^{-2}$ mol/L, such that $3.16 \times 10^{-4}$ mol/L≤[HO⁻]≤$3.16 \times 10^{-2}$ mol/L.

In one embodiment, the catalyst in the process according to the invention is an inorganic base.

In one embodiment, the inorganic base in the process according to the invention is chosen from the group consisting of soda (sodium hydroxide) or potash (potassium hydroxide).

In one embodiment, the concentration by weight of the inorganic base in the process according to the invention is between $1.2 \times 10^{-5}$% and 1.3%.

In one embodiment, the concentration by weight of the inorganic base in the process according to the invention is between 0.25% and 1.1%.

In one embodiment, the concentration by weight of the inorganic base in the process according to the invention is 1%.

In one embodiment, the concentration by weight of the inorganic base in the process according to the invention is 0.5%.

In one embodiment, the catalyst in the process according to the invention is an organic base.

In one embodiment, the organic base in the process according to the invention is pyridine.

In one embodiment, the pH of the aqueous reaction medium in the process according to the invention is basic.

In one embodiment, the pH of the aqueous reaction medium in the process according to the invention is within a range from 8 to 13.5.

In one embodiment, the pH of the aqueous reaction medium in the process according to the invention is within a range from 10.5 to 12.5.

In one embodiment, the catalyst in the process according to the invention is an acid.

In this embodiment, the reactive functional group of the catalyst is the $H_3O^+$ ion.

In one embodiment, the concentration of catalyst $H_3O^+$ in the process according to the invention is between $3.16 \times 10^{-7}$ mol/L and 0.01 mol/L, such that $3.16 \times 10^{-7}$ mol/L ≤ $[H_3O^-] \leq 0.01$ mol/L.

In one embodiment, the concentration of catalyst $H_3O^+$ in the process according to the invention is between $10^{-6}$ mol/L and $3.16 \times 10^{-5}$ mol/L, such that $10^{-6}$ mol/L ≤ $[H_3O^+] \leq 3.16 \times 10^{-5}$ mol/L.

In the aqueous phase, the situation is that pH=−log $([H_3O^+])$ and $[H_3O^+] = 10^{-pH}$.

In one embodiment, the acid in the process according to the invention is an inorganic acid.

In one embodiment, the inorganic acid in the process according to the invention is hydrochloric acid.

In one embodiment, the concentration by weight of the inorganic acid in the process according to the invention is between $1.14 \times 10^{-5}$% and 1.15%.

In one embodiment, the concentration by weight of the inorganic acid in the process according to the invention is between 0.05% and 1%.

In one embodiment, the concentration by weight of the inorganic acid in the process according to the invention is between 0.05% and 0.36%.

In one embodiment, the catalyst in the process according to the invention is an organic acid.

In one embodiment, the organic acid is chosen from the group consisting of glutamic acid and acetic acid.

In one embodiment, the concentration by weight of the organic acid in the process according to the invention is between 0.25% and 2%.

In one embodiment, the concentration by weight of the organic acid in the process according to the invention is between 0.25% and 1.1%.

In one embodiment, the concentration by weight of the organic acid in the process according to the invention is 1%.

In one embodiment, the pH of the aqueous reaction medium in the process according to the invention is acidic.

In one embodiment, the pH of the aqueous reaction medium in the process according to the invention is within a range from 2 to 6.5.

In one embodiment, the pH of the aqueous reaction medium in the process according to the invention is within a range from 4.5 to 6.

The basic or acidic catalyst is soluble in an aqueous medium.

In one embodiment, the polysaccharide in the process according to the invention is chosen from the group consisting of hyaluronic acid or one of its salts, chitosan, cellulose and their derivatives.

In one embodiment, the polysaccharide is hyaluronic acid.

In one embodiment, the polysaccharide is sodium hyaluronate.

In one embodiment, the polysaccharide is chitosan.

In one embodiment, the chitosan is partially deacetylated.

In one embodiment, a chitosan with a degree of deacetylation of approximately 80% is used.

In one embodiment, the polysaccharide is cellulose or one of its derivatives.

In one embodiment, the polysaccharide is carboxymethylcellulose.

The term Mw or "molecular weight" is used to describe the weight-average molecular weight of the polysaccharide, measured in daltons.

In one embodiment, the molecular weight of the polysaccharide is within a range from 0.01 MDa to 4.0 MDa.

In one embodiment, the molecular weight of the polysaccharide is within a range from 0.1 MDa to 3.6 MDa.

In one embodiment, the molecular weight of the polysaccharide is within a range from 0.10 MDa to 0.15 MDa.

In one embodiment, the molecular weight of the polysaccharide is within a range from 0.9 MDa to 2 MDa.

In one embodiment, the molecular weight of the polysaccharide is within a range from 2.5 to 3.6 MDa.

In one embodiment, the molecular weight Mw of the polysaccharide is 2.7 MDa.

In one embodiment, the molecular weight Mw of the polysaccharide is 1.5 MDa.

In one embodiment, the molecular weight Mw of the polysaccharide is 1.0 MDa.

In one embodiment, the molecular weight Mw of the polysaccharide is 120 000 Da.

In one embodiment, the crosslinking agent in the process according to the invention is bi- or polyfunctional.

In one embodiment, the bi- or polyfunctional crosslinking agent in the process according to the invention has at least one epoxide functional group.

In one embodiment, the bi- or polyfunctional crosslinking agent in the process according to the invention is chosen from the group consisting of ethylene glycol diglycidyl ether, butanediol diglycidyl ether, polyglycerol polyglycidyl ether, polyethylene glycol diglycidyl ether, polypropylene glycol diglycidyl ether, a bisepoxy or a polyepoxy, such as 1,2,3,4-diepoxybutane or 1,2,7,8-diepoxyoctane.

In one embodiment, the bi- or polyfunctional crosslinking agent in the process according to the invention is epichlorohydrin.

In one embodiment, the bi- or polyfunctional crosslinking agent in the process according to the invention has at least one vinyl functional group.

In one embodiment, the bi- or polyfunctional crosslinking agent in the process according to the invention is a dialkyl sulfone wherein the identical or different and linear or branched alkyl groups are chains having from 1 to 4 carbon atoms.

In one embodiment, the bi- or polyfunctional crosslinking agent in the process according to the invention is divinyl sulfone.

In one embodiment, the crosslinking agent in the process according to the invention is a mono-, bi- or polyaldehyde.

In one embodiment, the crosslinking agent in the process according to the invention is formaldehyde.

In one embodiment, the crosslinking agent in the process according to the invention is glutaraldehyde.

In one embodiment, the molar ratio of the crosslinking agent to the polysaccharide employed in the process according to the invention is within a range from 0.001 to 0.5.

In one embodiment, the molar ratio of the crosslinking agent to the polysaccharide employed in the process according to the invention is within a range from 0.01 to 0.3.

In one embodiment, the molar ratio of the crosslinking agent to the polysaccharide employed in the process according to the invention is within a range from 0.05 to 0.2.

In one embodiment, the molar ratio of the crosslinking agent to the polysaccharide employed in the process according to the invention is equal to 0.07.

In one embodiment, the molar ratio of the crosslinking agent to the polysaccharide employed in the process according to the invention is equal to 0.08.

In one embodiment, the molar ratio of the crosslinking agent to the polysaccharide employed in the process according to the invention is equal to 0.10.

In one embodiment, the molar ratio of the crosslinking agent to the polysaccharide employed in the process according to the invention is equal to 0.14.

In one embodiment, the molar ratio of the crosslinking agent to the polysaccharide employed in the process according to the invention is equal to 0.21.

In one embodiment, the precursor of the substituent in the process according to the invention is chosen from the group of the molecules comprising just one reactive functional group chosen from the group consisting of vinyl, epoxide, allyl, ketone, aldehyde, thiocyanate, halide, isocyanate, halosilicon, nitrile and sultone functional groups.

The term "reactive functional group" is understood to mean a functional group capable of forming a bond with a hydroxyl functional group of the polysaccharide.

In one embodiment, the bond is formed by creation of an ether bond.

In one embodiment, the bond is formed by creation of a hemiacetal bond.

In one embodiment, the bond is formed by the creation of a urethane bond.

Under the conditions of the process according to the invention, the formation of an ester functional group is thus excluded.

In one embodiment, the precursor of the substituent in the process according to the invention is chosen from the group consisting of molecules additionally comprising at least one advantageous functional group or group, inert with regard to the substitution and crosslinking reactions, chosen from the group consisting of sulfonate, linear or branched alkyl, substituted or unsubstituted aromatic, sulfate, thiol, monosaccharide, phosphate, phosphonate, carbonate and ester groups or functional groups.

The term "inert" is understood to mean a functional group which does not react under the conditions of implementation of the process and which is stable under the conditions of storage of the product obtained according to the process of the invention. A functional group which, under the conditions of implementation of the process, would be capable of not reacting with any of the functional groups of the polysaccharide or with any of the functional groups of the crosslinking agent or with any of the reactive functional groups of the precursor of the substituent is thus inert under the conditions of implementation of the process.

In one embodiment, the precursor of the substituent in the process according to the invention is chosen from the group consisting of the molecules of general formula F—R-(G)$_x$, wherein:
  F is a reactive functional group chosen from the group consisting of substituted or unsubstituted vinyl, substituted or unsubstituted epoxide, substituted or unsubstituted allyl, ketone, aldehyde, thiocyanate, halide, isocyanate, halosilicon, nitrile and sultone functional groups;
  R is a bond or an alkyl chain having from 1 to 12 carbon atoms, linear or branched, substituted or unsubstituted aromatic, saturated or unsaturated, optionally comprising one or more heteroatoms;
  G is either a hydrogen or an advantageous functional group or group, which are inert, chosen from the group consisting of the sulfonate, linear or branched alkyl, substituted or unsubstituted aromatic, sulfate, thiol, monosaccharide, phosphate, phosphonate, carbonate and ester groups or functional groups;
  x is a natural integer such that $1 \leq x \leq 3$.

In one embodiment, F in the process according to the invention is a vinyl functional group and the precursor of the substituent is chosen from the group consisting of compounds of formula:

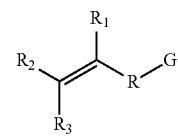

R and G being as defined above,
$R_1$, $R_2$ and $R_3$, which are identical or different, being either a hydrogen atom or an alkyl chain having from 1 to 3 carbon atoms.

In one embodiment, F in the process according to the invention is an epoxide functional group and the precursor of the substituent is chosen from the group consisting of compounds of formula:

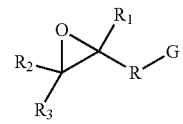

R and G being as defined above,
$R_1$, $R_2$ and $R_3$ being as defined above.

In one embodiment, F in the process according to the invention is an allyl functional group and the precursor of the substituent is chosen from the group consisting of compounds of formula:

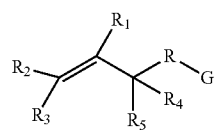

R and G being as defined above,
$R_1$, $R_2$ and $R_3$ being as defined above,
$R_4$ and $R_5$, which are identical or different, being either a hydrogen atom or an alkyl chain having from 1 to 3 carbon atoms.

In one embodiment, G in the process according to the invention is a sulfate functional group.

In one embodiment, G in the process according to the invention is a hydrogen atom.

In one embodiment, G in the process according to the invention is a sulfonate functional group.

In one embodiment, the precursor of the substituent in the process according to the invention is chosen from the group consisting of allyl-sulfates, epoxy-sulfates, vinyl-sulfonates and epoxy-alkanes.

In one embodiment, the substituent in the process according to the invention is chosen from the group consisting of vinylsulfonic acid and its salts, epoxybutane and sodium allyl sulfate.

In one embodiment, the polyfunctional crosslinking agent in the process according to the invention is 1,4-butanediol diglycidyl ether (BDDE) and the precursor of the substituent is sodium vinylsulfonate.

In one embodiment, the polyfunctional crosslinking agent in the process according to the invention is 1,4-butanediol diglycidyl ether (BDDE) and the precursor of the substituent is sodium allyl sulfate.

In one embodiment, the polyfunctional crosslinking agent in the process according to the invention is 1,4-butanediol diglycidyl ether (BDDE) and the precursor of the substituent is epoxybutane.

In one embodiment, the polyfunctional crosslinking agent in the process according to the invention is divinyl sulfone and the precursor of the substituent is sodium vinylsulfonate.

In one embodiment, the molar ratio of the precursor of the substituent to the polysaccharide employed in the process according to the invention is within a range from 0.001 to 4.00.

In one embodiment, the molar ratio of the precursor of the substituent to the polysaccharide employed in the process according to the invention is within a range from 0.20 to 2.20.

In one embodiment, the molar ratio of the precursor of the substituent to the polysaccharide employed in the process according to the invention is equal to 0.24.

In one embodiment, the molar ratio of the precursor of the substituent to the polysaccharide employed in the process according to the invention is equal to 0.30.

In one embodiment, the molar ratio of the precursor of the substituent to the polysaccharide employed in the process according to the invention is equal to 0.35.

In one embodiment, the molar ratio of the precursor of the substituent to the polysaccharide employed in the process according to the invention is equal to 0.90.

In one embodiment, the molar ratio of the precursor of the substituent to the polysaccharide employed in the process according to the invention is equal to 1.00.

In one embodiment, the molar ratio of the precursor of the substituent to the polysaccharide employed in the process according to the invention is equal to 1.60.

In one embodiment, the molar ratio of the precursor of the substituent to the polysaccharide employed in the process according to the invention is equal to 2.00.

Principally, the crosslinking and substitution reactions in the process according to the invention are carried out simultaneously, under the same experimental conditions and on the same reaction sites of the polysaccharide, this being the case without there being competition between the various entities involved. The degrees of substitution and crosslinking are the same as those of the reactions carried out in isolation.

The process thus makes it possible to be able to control the crosslinking independently of the substitution in order to facilitate the preparation of the gels and to be able to easily adapt the product according to the use thereof.

The present invention, because the substitution and the crosslinking are simultaneous, makes it possible to limit the time during which the polysaccharide is present in an alkaline medium which decomposes it if residence is prolonged. Specifically, it is well known that, in the case of a simple substitution in an alkaline medium, for example, hyaluronic acid is rapidly decomposed and loses all its gelling and viscoelastic properties. A surprising effect of the invention is that the fact that the crosslinking and substitution reactions are simultaneous protects the polysaccharide during the reaction and makes it possible to obtain a synergistic effect with regard to the rheological properties, in particular the elasticity of the polysaccharide, which is greatly increased.

The advantages related to the fact that the crosslinking/substitution reactions are simultaneous are not limited to advantages visible on the final product, such as a better elasticity, a good homogeneity of the gel, homogeneous distribution of the substituents or the limitation of the decomposition of the polysaccharide during the crosslinking/substitution, but also comprise the reaction time and in particular the number of reaction steps. The process of the invention makes possible simultaneous introduction of all the reactants. Just one single reaction step offers not only a considerable saving in time but also limits losses of time and of solvents. As all the reactions involved, namely crosslinking and substitution reactions, take place under the same conditions, the catalyst introduced will be active for both reactions without it being necessary to increase its amount in comparison with a simple crosslinking. The absence of competition between crosslinking and substitution prevents it from being necessary to add an excess of reactant in order to compensate for the decomposition thereof or the excessively rapid consumption thereof.

The process of the invention does not use catalysts other than simple acids or bases, does not use organic solvents and does not use activating agents, and the atomic balance of the reaction is good, given the absence of formation of byproducts.

The latter point is the other advantage of the invention: the process of the invention does not produce byproducts which have to be removed during the purification. It is simply a matter of rinsing the product in order to remove the excess crosslinking agent and catalyst. In view of the applications of the polysaccharides obtained, in particular as biomaterials, this absence of byproducts is a real competitive advantage.

The process which makes it possible to obtain the compounds of the present invention differs from the prior art in that the simple implementation thereof makes it possible, surprisingly, to substitute and crosslink a polysaccharide simultaneously without the substitution being in competition with the crosslinking. Better control is thus exercised over the degree of crosslinking or the degree of substitution.

The process which makes it possible to obtain the products of the present invention offers complete freedom with regard to the parametering of each of the reactions occurring simultaneously and independently in the reaction medium. It is thus possible to modify the degree of crosslinking without influencing the substitution and, conversely, it is possible to modify the degree of substitution without influencing the crosslinking.

The implementation of the crosslinking process of the invention makes it possible to obtain a product of high homogeneity which can be easily injected. Surprisingly, the process according to the invention makes it possible to enhance the rheological properties of the crosslinked polysaccharides without having to employ more crosslinking agent. In addition, it makes it possible to introduce other properties, such as hydration or lipophilicity.

The process of the invention is such that it is possible to envisage carrying out up to three reactions simultaneously. The term "three simultaneous reactions" is understood to mean a crosslinking simultaneously with a double substitution.

In one embodiment, the polysaccharide obtained by the process according to the invention is substituted on its hydroxyl functional groups.

The degree of substituent introduced (DSI) is defined as being:

$$DSI = \frac{\text{(Number of moles of reactive \textit{fonctional} groups of the substituent introduced into the reaction medium)}}{\text{(Number of moles of disaccharide unit introduced into the reaction medium)}}$$

In one embodiment, the degree of substituent introduced in the process according to the invention is within a range from 0.001 to 4.00 (0.001≤DSI≤4.00).

In one embodiment, the degree of substituent introduced in the process according to the invention is within a range from 0.20 to 2.20 (0.20≤DSI≤2.20).

In one embodiment, the degree of substituent introduced in the process according to the invention is equal to 0.24.

In one embodiment, the degree of substituent introduced in the process according to the invention is equal to 0.30.

In one embodiment, the degree of substituent introduced in the process according to the invention is equal to 0.35.

In one embodiment, the degree of substituent introduced in the process according to the invention is equal to 0.90.

In one embodiment, the degree of substituent introduced in the process according to the invention is equal to 1.00.

In one embodiment, the degree of substituent introduced in the process according to the invention is equal to 1.60.

In one embodiment, the degree of substituent introduced in the process according to the invention is equal to 2.00.

In one embodiment, the polysaccharide obtained in the process according to the invention is crosslinked by the reaction of the crosslinking agent with its hydroxyl functional groups.

The degree of crosslinking agent introduced (DCI) is defined as being:

$$DCI = \frac{\text{(Number of moles crosslinking agent introduced into the reaction medium)}}{\text{(Number of moles \textit{disacharide} unit introduced into the reaction medium)}}$$

In one embodiment, the degree of crosslinking agent introduced in the process according to the invention is within a range from 0.001 to 0.5.

In one embodiment, the degree of crosslinking agent introduced in the process according to the invention is within a range from 0.01 to 0.3.

In one embodiment, the degree of crosslinking agent introduced in the process according to the invention is 0.07.

In one embodiment, the degree of crosslinking agent introduced in the process according to the invention is 0.08.

In one embodiment, the degree of crosslinking agent introduced in the process according to the invention is 0.10.

In one embodiment, the degree of crosslinking agent introduced in the process according to the invention is 0.14.

In one embodiment, the degree of crosslinking agent introduced in the process according to the invention is 0.21.

In one embodiment, the ratio of the weight of polysaccharide employed to the weight of water employed in the process according to the invention is within a range from 4% to 20%, as percentage by weight.

In one embodiment, the ratio of the weight of polysaccharide employed to the weight of water employed in the process according to the invention is within a range from 6% to 16%, as percentage by weight.

In one embodiment, the ratio of the weight of polysaccharide employed to the weight of water employed in the process according to the invention is within a range from 8% to 14%, as percentage by weight.

In one embodiment, the ratio of the weight of polysaccharide employed to the weight of water employed in the process according to the invention is 5.7%, as percentage by weight.

In one embodiment, the ratio of the weight of polysaccharide employed to the weight of water employed in the process according to the invention is 6.3%, as percentage by weight.

In one embodiment, the ratio of the weight of polysaccharide employed to the weight of water employed in the process according to the invention is 10.3%, as percentage by weight.

In one embodiment, the ratio of the weight of polysaccharide employed to the weight of water employed in the process according to the invention is 11.1%, as percentage by weight.

In one embodiment, the ratio of the weight of polysaccharide employed to the weight of water employed in the process according to the invention is 12.2%, as percentage by weight.

In one embodiment, the ratio of the weight of polysaccharide employed to the weight of water employed in the process according to the invention is 13.5%, as percentage by weight.

In one embodiment, the ratio of the weight of polysaccharide employed to the weight of water employed in the process according to the invention is 14.3%, as percentage by weight.

In one embodiment, the ratio of the weight of polysaccharide employed to the weight of water employed in the process according to the invention is 15.8%, as percentage by weight.

In one embodiment, the process according to the invention is carried out at room temperature.

The term "room temperature" is understood to mean a temperature between 18° C. and 25° C.

In one embodiment, the process according to the invention is carried out at a temperature of greater than 25° C.

In one embodiment, the process according to the invention is carried out at a temperature of less than 60° C.

In one embodiment, the process according to the invention is carried out at a temperature of between 39° C. and 60° C.

In one embodiment, the process according to the invention is carried out at a temperature of 40° C.

In one embodiment, the process according to the invention is carried out at a temperature of 50° C.

In one embodiment, the process according to the invention is carried out for a period of time within a range from 15 minutes to 48 hours.

In one embodiment, the process according to the invention is carried out for a period of time of 1 to 2 hours.

In one embodiment, the process according to the invention is carried out for a period of time of 2 to 3 hours.

In one embodiment, the process according to the invention is carried out for a period of time of 3 to 4 hours.

In one embodiment, the process according to the invention is carried out for a period of time of 4 to 5 hours.

In one embodiment, the process according to the invention additionally comprises a step of washing the polysaccharide obtained.

In one embodiment, the process according to the invention additionally comprises a step of washing the polysaccharide obtained with a buffer solution having a pH of approximately 7.

In one embodiment, the process according to the invention additionally comprises a step of washing the polysaccharide obtained with purified water.

In one embodiment, the crosslinking of the polysaccharide in the product obtained according to the process of the invention is carried out by dialiyldialkyl sulfone bridges of formula PS—O—(CH2)n-S(O2)-(CH2)n-O—PS, where "PS" represents the polysaccharide residue and n represents an integer such that 1≤n≤4.

In one embodiment, the crosslinking of the polysaccharide in the product obtained according to the process of the invention is carried out by diethyl sulfone bridges of formula PS—O—$CH_2$—$CH_2$—$S(O_2)$—$CH_2$—$CH_2$—O—PS.

In one embodiment, the crosslinking of the polysaccharide in the product obtained according to the process of the invention is carried out by bridges of formula PS—O—$CH_2$—CH(OH)—$CH_2$—X—$CH_2$—CH(OH)—$CH_2$—O—PS, the X group being either an alkyl chain having from 2 to 6 carbon atoms or a polyether chain.

In one embodiment, the crosslinking of the polysaccharide in the product obtained according to the process of the invention is carried out by ether bridges of formula PS—O—$CH_2$—O—PS.

In one embodiment, the crosslinking of the polysaccharide in the product obtained according to the process of the invention is carried out by hemiacetal bridges of formula PS—O—CH(OH)—$(CH_2)_m$—CH(OH)—O—PS, where m is an integer such that 0≤m≤4.

In one embodiment, the polysaccharide in the product obtained according to the process of the invention carries, on at least one of its hydroxyl functional groups, at least one substituent resulting from vinylsulfonic acid, 2-ethoxyethylsulfonic acid.

In one embodiment, the polysaccharide in the product obtained according to the process of the invention carries, on at least one of its hydroxyl functional groups, at least one substituent resulting from epoxybutane, 1-ethoxybutan-2-ol.

In one embodiment, the polysaccharide in the product obtained according to the process of the invention carries, on at least one of its hydroxyl functional groups, at least one substituent resulting from sodium allyl sulfate, sodium 3-propoxy sulfate.

The invention relates to the use of a hydrogel obtained according to the process of the invention in the formulation of a viscosupplementation composition.

The process according to the invention also relates to the compositions comprising a polysaccharide obtained by the process according to the invention.

In one embodiment, the polysaccharide obtained by the process according to the invention is in the gel or hydrogel form.

On conclusion of the crosslinking and substitution, it may be advantageous to neutralize the gel obtained according to standard processes known in the field, for example by addition of acid, when the process is carried out in a basic medium, and by addition of a base, when the process is carried out in an acidic medium.

The mixture obtained on conclusion of the process of the invention can optionally be subjected to an additional hydration step, in order to obtain a gel in the form of an injectable hydrogel suitable for the applications envisaged.

This hydration is generally carried out, in an aqueous medium, by simple mixing of the crosslinked and substituted gel with an aqueous solution, advantageously a buffered physiological aqueous solution, so as to obtain a final concentration which can vary within very wide proportions, according to the nature of the polysaccharides used, according to their respective degrees of crosslinking and also according to the use envisaged. The buffered solution which can be used can, for example, be an iso-osmolar physiological solution exhibiting a pH of between approximately 6.8 and approximately 7.5.

This final concentration of total polysaccharides is generally between approximately 5 and approximately 100 mg/g, preferably between approximately 5 and approximately 50 mg/g, for example approximately 20 mg/g, of hydrogel.

The invention relates to the use of a polysaccharide obtained according to the process of the invention in the formulation of a viscosupplementation composition.

The invention relates to the use of a polysaccharide obtained according to the process of the invention in the formulation of a composition for filling in wrinkles.

The applications targeted are more particularly the applications commonly observed in the context of injectable polysaccharide viscoelastic products used or which can potentially be used in the following pathologies or treatments:
  cosmetic injections: for filling in wrinkles, skin defects or defects Of volume (cheekbones, chins, lips);
  treatment of osteoarthritis, injection into the joint to replace or supplement deficient synovial fluid;
  periurethral injection in the treatment of urinary incontinence by sphincter insufficiency;
  postsurgical injection for preventing peritoneal adhesions in particular;
  injection subsequent to surgery for far-sightedness by scleral incisions using a laser;
  injection into the vitreous cavity.

More particularly, in cosmetic surgery, according to its viscoelastic properties and properties of persistence, the hydrogel obtained according to the process of the invention can be used:
  for filling in fine, moderate or deep wrinkles and can be injected with thin needles (27-gauge, for example);
  as volumizing product with injection via needles with a larger diameter, for example from 22- to 26-gauge, and with a greater length (30 to 40 mm, for example); in this case, its cohesive nature will make it possible to guarantee that it is maintained at the site of the injection.

The polysaccharide obtained according to the process of the invention also has an important application in joint surgery and in dental surgery for filling in periodontal pockets, for example.

These implementational examples are in no way limiting, the polysaccharide obtained according to the process of the present invention being more widely provided for:
  filling in volumes;
  generating spaces within certain tissues, thus promoting their optimum functioning;
  replacing deficient physiological fluids.

The polysaccharide obtained according to the process of the invention also has an application in the preparation of bone substitutes.

The polysaccharide obtained according to the process of the invention can also have an entirely advantageous application as matrix for releasing one (or more) active principle(s) dispersed beforehand within it. The term "active principle" is understood to mean any product which is active pharmacologically: medicinal active principle, antioxidant active principle (sorbitol, mannitol, and the like), antiseptic active principle, anti-inflammatory active principle, local anesthetic active principle (lidocaine, and the like), and the like.

In practice, the polysaccharide obtained according to the process of the invention, preferably after purification and hydration to give the hydrogel, can be packaged, for example in syringes, and sterilized according to any means known per se (for example by autoclaving) in order to be sold and/or used directly.

According to another aspect, the present invention relates to a kit comprising a polysaccharide obtained according to the process of the invention packaged in a sterile syringe.

The characteristics of the polysaccharides obtained according to the process of the invention are demonstrated in the examples below.

DETAILED DESCRIPTION

Examples

Figure 1:
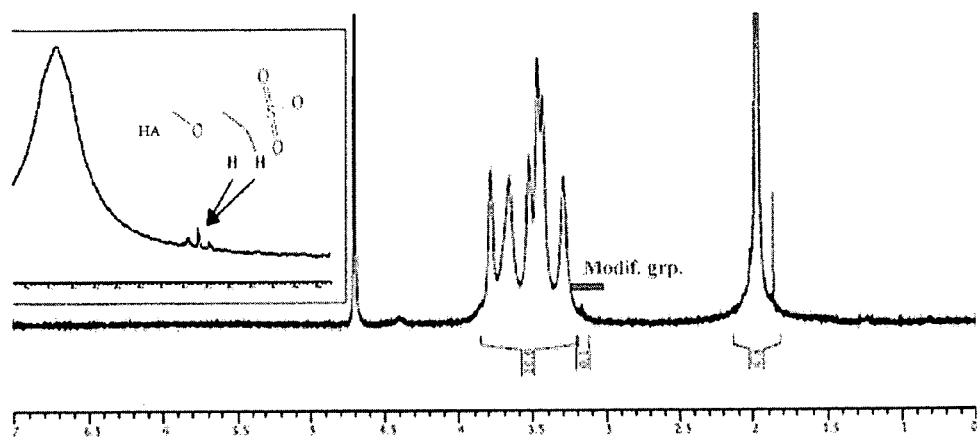
FIG. 1: NMR spectrum of the gel G1A.

The degrees of substituent introduced (DSI), degree of crosslinking agent introduced (DCI) and reactive catalyst ratio in the examples which follow are defined by:

Degree of Crosslinking Agent Introduced:

DCI=Number of moles of crosslinking agent introduced into the reaction medium/number of moles of disaccharide unit introduced into the reaction medium Degree of Substituent Introduced:

DSI=Number of moles of reactive functional groups of the substituent introduced into the reaction medium/number of moles of disaccharide unit introduced into the reaction medium Reactive Catalyst Ratio RCR=Number of moles of reactive functional groups of the catalyst introduced into the reaction medium/number of moles of disaccharide unit introduced into the reaction medium Example 1

Demonstration of the Synergistic Effect with Regard to the Rheological Properties of the Substitution Carried Out Simultaneously with the Crosslinking The following steps are described below:

Substitution of VSA (sodium salt of vinylsulfonic acid) on noncrosslinked NaHA (sodium hyaluronate)

Characterization of the substitution

Crosslinking of NaHA by BDDE (1,4-butanediol diglycidyl ether)

Substitution of VSA (sodium salt of vinylsulfonic acid) on NaHA simultaneously with crosslinking by BDDE (1,4-butanediol diglycidyl ether)

Substitution of VSA (sodium salt of vinylsulfonic acid) on NaHA followed by crosslinking by BDDE (1,4-butanediol diglycidyl ether)

Demonstration of the synergistic effect on the rheological properties introduced by the substitution carried out simultaneously with the crosslinking Gel G1A Synthesis: Substitution of VSA (Sodium Salt of Vinylsulfonic Acid) on Noncrosslinked NaHA, at a Temperature of 50° C. and in an Alkaline Medium (RCR=0.8:1)

Step a): Hydration of sodium hyaluronate fibers in the form of a noncrosslinked gel Sodium hyaluronate fibers of injectable grade (0.9 g, i.e. 2.24 mmol; molecular weight: approximately 2.7 MDa) are weighed out in a container. A 1% aqueous solution of sodium hydroxide (0.25 mol/L, i.e. 1.85 mmol of $HO^-$ introduced into the medium) in water (7.4 g) is added (RCR=0.8:1) and the combined mixture is homogenized for approximately 1 hour using a spatula at room temperature and 900 mmHg.

Step b): Substitution

VSA (102 mg, i.e. 0.78 mmol) is added to the noncrosslinked sodium hyaluronate (NaHA) gel obtained in the preceding step, the combined mixture being homogenized with a spatula for approximately 30 minutes at a temperature of 12-14° C. The combined mixture is subsequently placed on a water bath at 50° C. for 2 h 10. The degree of substituent introduced DSI is equal to approximately 0.35.

Step c): Neutralization, Purification

The substituted final gel is subsequently neutralized by addition of 1N HCl and placed in a phosphate buffer bath in order to stabilize the pH and to make possible the hydration or swelling thereof in order to obtain a gel comprising 20 mg/g of HA (hyaluronic acid). This gel is subsequently homogenized before being packaged in syringes which are sterilized by autoclaving. A substituted and sterilized NaHA hydrogel G1A is thus obtained.

Gel REF1A Synthesis

The gel REF1A is synthesized according to the procedure for gel G1A described above, the VSA being replaced with water for parenteral injection (WPI).

Characterization of the Chemical Modifications to the Gels G1A and REF1A by Liquid $^1H$ NMR The NMR spectrum of the gel G1A is represented in FIG. 1.

Figure 2:
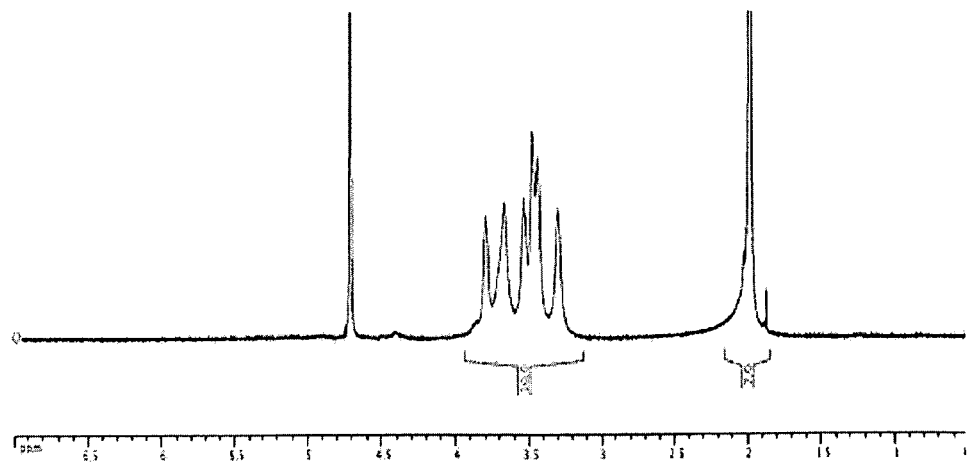
FIG. 2: NMR spectrum of the gel REF1A. Comparison to FIG. 1 confirms the chemical substitution (via a covalent bond) of the VSA on the hydroxyl functional group of the NaHA.

The NMR spectrum of the gel REF1A is represented in FIG. 2.

Comparison of the spectra of FIGS. 1 and 2 makes it possible to confirm the chemical substitution (via a covalent bond) of the VSA on the hydroxyl functional group of the NaHA.

Gel G1B Synthesis: Crosslinking of NaHA by BDDE (1,4-Butanediol Diglycidyl Ether), at a Temperature of 50° C. and in an Alkaline Medium (RCR=0.8:1)

Step a): Identical to step a) of the synthesis of the gel G1A

Step b): Crosslinking

BDDE (65 mg, i.e. 0.32 mmol) is added to the noncrosslinked sodium hyaluronate (NaHA) gel obtained in the preceding step, the combined mixture being homogenized using a spatula for approximately 30 minutes at a temperature of 12-14° C. The combined mixture is subsequently placed on a water bath at 50° C. for 2 h 10. The degree of crosslinking agent introduced DCI is equal to approximately 0.14.

Step c): Neutralization, Purification

The crosslinked final gel is subsequently neutralized by the addition of 1N HCl and placed in a phosphate buffer bath in order to stabilize the pH and to make possible the hydration or swelling thereof in order to obtain a gel comprising 20 mg/g of HA. This gel is subsequently homogenized before being filled into syringes which are sterilized by autoclaving. A crosslinked and sterilized NaHA hydrogel G1B is thus obtained.

Gel G1C Synthesis: Substitution of VSA (Sodium Salt of Vinylsulfonic Acid) on NaHA Simultaneously with Crosslinking by BDDE (1,4-Butanediol Diglycidyl Ether), at a Temperature of 50° C. and in an Alkaline Medium (RCR=0.8:1)

Step a): Identical to Step a) of the Synthesis of the Gel G1A

Step b): Crosslinking and Substitution

BDDE (65 mg, i.e. 0.32 mmol) and VSA (102 mg, i.e. 0.78 mmol) are added to the noncrosslinked sodium hyaluronate (NaHA) gel obtained in the preceding step, the combined mixture being homogenized using a spatula for approximately 30 minutes at a temperature of 12-14° C. The combined mixture is subsequently placed on a water bath at 50° C. for 2 h 10. The degree of crosslinking agent introduced DCI is equal to approximately 0.14 and the degree of substituent introduced DSI is equal to approximately 0.35.

Step c): Neutralization, Purification

The crosslinked and substituted final gel is subsequently neutralized by the addition of 1N HCl and placed in a phosphate buffer bath in order to stabilize the pH and to make possible the hydration or swelling thereof in order to obtain a gel comprising 20 mg/g of HA. This gel is subsequently homogenized before being packaged in syringes which are sterilized by autoclaving. A crosslinked, substituted and sterilized NaHA hydrogel G1C is thus obtained.

Gel G1D synthesis: Substitution of VSA (sodium salt of vinylsulfonic acid) on NaHA followed by crosslinking by BDDE (1,4-butanediol diglycidyl ether), at a temperature of 40° C. and in an alkaline medium (RCR=0.8:1)

Step a): Identical to step a) of the synthesis of the gel G1A

Step b): Substitution

VSA (102 mg, i.e. 0.78 mmol) is added to the non-crosslinked sodium hyaluronate (NaHA) gel obtained in the preceding step, the combined mixture being homogenized using a spatula for approximately 30 minutes at a temperature of 12-14° C. The combined mixture is subsequently placed on a water bath at 40° C. for 1 h 00. The degree of substituent introduced DSI is equal to approximately 0.35. The time and the temperature were reduced in comparison with the G1A test in order to retain a gel thick enough for the following crosslinking step.

Step c): Crosslinking

BDDE (65 mg, i.e. 0.32 mmol) is added to the non-crosslinked substituted sodium hyaluronate (NaHA) gel obtained in the preceding step, the combined mixture being homogenized using a spatula for approximately 30 minutes at a temperature of 12-14° C. The combined mixture is subsequently placed on a water bath at 50° C. for 2 h 10. The degree of crosslinking agent introduced DCI is equal to approximately 0.14.

Step d): Neutralization, Purification

The crosslinked and substituted final gel is subsequently neutralized by the addition of 1N HCl and placed in a phosphate buffer bath in order to stabilize the pH and to make possible the hydration or swelling thereof in order to obtain a gel comprising 20 mg/g of HA. This gel is subsequently homogenized before being packaged in syringes which are sterilized by autoclaving. A substituted, then crosslinked and sterilized NaHA hydrogel G1D is thus obtained.

Demonstration of the Synergistic Effect on the Rheological Properties Introduced by the Substitution Simultaneously with the Crosslinking The viscosity n of the sterile gels is characterized on a TA Instruments AR 2000 Ex rheometer, under controlled stress conditions at 25° C. The viscosity value is recorded at a stress of $0.02 \text{ s}^{-1}$.

The elastic component G' and the viscous component G" of the sterile gels are characterized on a TA Instruments AR 2000 Ex rheometer, in oscillation at 25° C., the values of the elastic and viscous components being recorded at a frequency of 1 Hz.

The rheological results are presented in table I below:

TABLE I

| | G1A | G1B | G1C | G1D |
|---|---|---|---|---|
| Viscosity: η (Pa · s) at $0.02 \text{ s}^{-1}$ | 7 | 1822 | 1959 | 1502 |
| Elastic component: G' (Pa) at 1 Hz | 0.5 | 107 | 131 | 78 |
| Viscous component: G" (Pa) at 1 Hz | 3 | 27 | 29 | 22 |

The substitution on a gel simultaneously with the crosslinking (G1C test) introduces superior viscoelastic properties in comparison with the gels:
  simply substituted (gel G1A),
  simply crosslinked (gel G1B),
  first substituted and then crosslinked (gel G1D).

Surprisingly, the substitution carried out simultaneously with a crosslinking synergistically improves the rheological properties of the gels obtained.

Example 2

VSA (Sodium Salt of Vinylsulfonic Acid) Substitution on NaHA Simultaneously with Crosslinking by BDDE (1,4-Butanediol Diglycidyl Ether), at a Temperature of 50° C. and in an Alkaline Medium (RCR=0.8:1)

This example makes it possible to demonstrate, by the measurement of the rheological properties:
  the substitution of the vinyl functional group on the NaHA during crosslinking and the difference in structure introduced by the substitution,
  the better resistance to radical decomposition of the substituted and crosslinked gel.

Gel G2 synthesis

Step a): Hydration of Sodium Hyaluronate Fibers in the Form of a Noncrosslinked Gel Sodium hyaluronate fibers of injectable grade (0.9 g, i.e. 2.24 mmol; molecular weight: approximately 2.7 MDa) are weighed out in a container. A 1% aqueous solution of sodium hydroxide (0.25 mol/L, i.e. 1.85 mmol of $HO^-$ introduced into the medium) in water (7.4 g) is added (RCR=0.8:1) and the combined mixture is homogenized for approximately 1 hour using a spatula at room temperature and 900 mmHg.

Step b): Crosslinking and Substitution

BDDE (65 mg, i.e. 0.32 mmol) and VSA (70 mg, i.e. 0.54 mmol) are added to the noncrosslinked sodium hyaluronate (NaHA) gel obtained in the preceding step, the combined mixture being homogenized using a spatula for approximately 30 minutes at a temperature of 12-14° C. The combined mixture is subsequently placed on a water bath at 50° C. for 2 h 10. The degree of crosslinking agent introduced DCI is equal to approximately 0.14 and the degree of substituent introduced DSI is equal to approximately 0.24.

Step c): Neutralization, Purification

The crosslinked and substituted final gel is subsequently neutralized by the addition of 1N HCl and placed in a phosphate buffer bath in order to stabilize the pH and to make possible the hydration or swelling thereof in order to obtain a gel comprising 20 mg/g of HA. This gel is subsequently homogenized before being packaged in syringes which are sterilized by autoclaving. A crosslinked, substituted and sterilized NaHA hydrogel G2 is thus obtained.

Gel REF2 synthesis

The gel REF2 is synthesized according to the procedure for the gel G2 described above, the VSA being replaced with water for parenteral injection (WPI).

Characterization of the Extrusion Force or "Injectability" and of the Elasticity of the Gels G2 and REF2

The extrusion force is characterized on a Mecmesin tensile/compression testing machine under a rate of compression of 50 mm/min with 27G ½" needles; the results are given in the table below.

The elasticity of the sterile gels is characterized on a TA Instruments AR 2000 Ex rheometer, in oscillation at 25° C., the value of the elasticity being recorded at a frequency of 1 Hz; the results are presented in table II below.

TABLE II

|  | G2 | REF2 |
|---|---|---|
| Extrusion force (N), 27G ½" needle, Rate 50 mm/min | 35 | 38 |
| Elasticity: G' (Pa) at 1 Hz | 116 | 105 |

The substitution makes it possible to obtain finished products of greater rheology (+10%) for levels of injectability which are slightly lower (−8%). These rheological data confirm the chemical modification to the NaHA and thus the substitution of the vinyl functional group on the NaHA during crosslinking.

Test on Radical Decomposition of the Gels G2 and REF2

The gels were also characterized by a test on radical decomposition in vitro at 37° C. This test makes it possible to simulate the subsequent persistence in vivo (intradermal, intra-articular, and the like) of the injected gels.

It was developed on the basis of the test described in the publication "*Antioxidant activities of sulfated polysaccharides from brown and red seaweeds*", Rocha de Souza, J. Appl. Phycol. (2007), 19, 153-160.

The gels are decomposed by the free radicals generated by the Fenton reaction between hydrogen peroxide and ferrous ions. The decomposition is monitored by rheology at 37° C., the complex viscosity being measured. The curves of the trend in the decomposition results for these 2 gels subsequently make it possible to evaluate the half-lives of these different gels (period of time necessary to have $n^* = n^*_0/2$, in minutes, with $n^*_0$=complex viscosity at $t_0$ of the gel characterized). The half-lives obtained are given in table III below.

TABLE III

|  | G2 | REF2 |
|---|---|---|
| Half-life (minutes) | 8.0 | 5.1 |

Thus, for an injectability which is slightly lower and which makes it possible to retain good control of the surgical action, the half-lives of the modified gels obtained according to the invention are longer, guaranteeing a greater time of persistence in vivo, this being the case even with the low degree of substitution tested.

Example 3

VSA (Sodium Salt of Vinylsulfonic Acid) Substitution on NaHA Simultaneously with Crosslinking by BDDE (1,4-Butanediol Diglycidyl Ether), at a Temperature of 50° C. and in an Alkaline Medium (RCR=0.8:1)

This example makes it possible to demonstrate by rheology the increase in elasticity introduced into the gel as a function of the degree of substitution.

Gel G3A and gel G3B Synthesis

The synthesis of the gels is identical to that of the gels G1C and G2, with the amounts of VSA adjusted to the tested degrees of substituent introduced; see table IV below.

TABLE IV

|  | DSI |
|---|---|
| G3A | 1.00 |
| G3B | 2.00 |

Characterization of the Elasticity of the Gels G3A and G3B

The elasticity of the gels is characterized on a TA Instruments AR 2000 Ex rheometer described in example 2; the results are given in table V below.

TABLE V

|  | G2 | G1C | G3A | G3B | REF2 |
|---|---|---|---|---|---|
| Degree of substituent introduced, DSI | 0.24 | 0.35 | 1.00 | 2.00 | — |
| Elasticity: G' (Pa) at 1 Hz | 116 | 131 | 199 | 213 | 105 |

Figure 3:
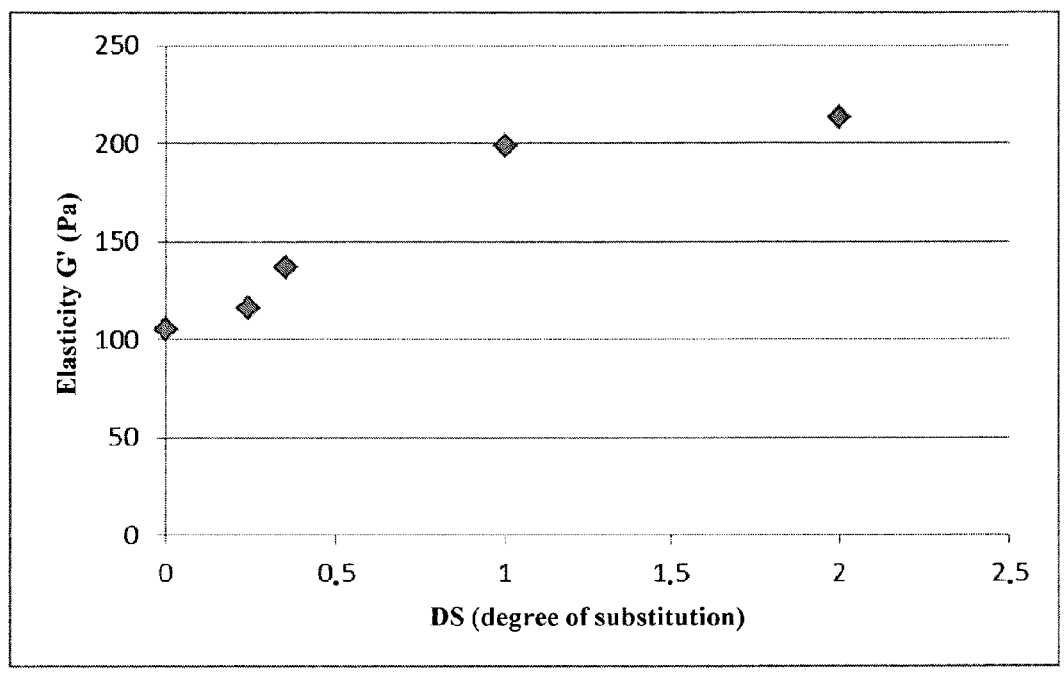
FIG. 3: Elasticity G' in Pa as a function of the degree of substitution (DS). The results represented in FIG. 3 show that the elasticity G' of the gels increases with the degree of substituent introduced: the chemical modification is indeed responsible for the optimization in the viscoelastic properties of the gels.

The results represented graphically in FIG. 3 show that the elasticity G' of the gels increases with the degree of substituent introduced: the chemical modification is indeed responsible for the optimization in the viscoelastic properties of the gels.

Example 4

EB (Epoxybutane) Substitution on NaHA Simultaneously with Crosslinking by BDDE (1,4-Butanediol Diglycidyl Ether), at a Temperature of 50° C. and in an Alkaline Medium (RCR=0.8:1)

This example makes it possible to demonstrate by rheology the substitution of an epoxy functional group on NaHA simultaneously with crosslinking.

Gel G4 Synthesis

Step a): Identical with Step a) of the Synthesis of the Gel G1A

Step b): Crosslinking and Substitution

BDDE (65 mg, i.e. 0.32 mmol) and EB (147 mg, i.e. 2.02 mmol) are added to the noncrosslinked sodium hyaluronate (NaHA) gel obtained in the preceding step, the combined mixture being homogenized using a spatula for approximately 30 minutes at a temperature of 12-14° C. The combined mixture is subsequently placed on a water bath at 50° C. for 2 h 10. The degree of crosslinking agent introduced DCI is equal to approximately 0.14 and the degree of substituent introduced DSI is equal to approximately 0.90.

Step c): Neutralization, Purification

The crosslinked and substituted final gel is subsequently neutralized by the addition of 1N HCl and placed in a phosphate buffer bath in order to stabilize the pH and to make possible the hydration or swelling thereof in order to obtain a gel comprising 20 mg/g of HA. This gel is subsequently homogenized before being packaged in syringes. A crosslinked, substituted and sterilized NaHA hydrogel G4 is thus obtained.

Gel REF4 Synthesis

The gel REF4 is synthesized according to the procedure for the gel G4 described above, the EB being replaced with water for parenteral injection (WPI).

Characterization of the Elasticity of the Gels G4 and REF4

The elasticity of the gels is characterized on the TA Instruments AR 2000 Ex rheometer described in example 2; the results are given in table VI below.

TABLE VI

|  | G4 | REF4 |
|---|---|---|
| Elasticity: G' (Pa) at 1 Hz | 180 | 150 |

The substitution of a molecule comprising an epoxy reactive group on the NaHA is confirmed by the rheological results: the chemical modification makes it possible to obtain finished products having a higher elasticity.

These rheological data confirm the substitution of the epoxide functional group on the NaHA during crosslinking.

Example 5

VSA (Sodium Salt of Vinylsulfonic Acid) Substitution on NaHA Simultaneously with Crosslinking by BDDE (1,4-Butanediol Diglycidyl Ether), at a Temperature of 50° C. and in an Alkaline Medium (RCR=0.7:1)

This example makes it possible to demonstrate by rheology the substitution on NaHA of low molecular weight.

Gel G5 Synthesis

Step a): Hydration of Sodium Hyaluronate Fibers in the Form of a Noncrosslinked Gel Sodium hyaluronate fibers of injectable grade (0.9 g, i.e. 2.24 mmol; molecular weight: approximately 1.5 MDa) are weighed out in a container. A 1% aqueous solution of sodium hydroxide (0.25 mol/L, i.e. 1.57 mmol of HO$^-$ introduced into the medium) in water (6.3 g) is added (RCR=0.7:1) and the combined mixture is homogenized for approximately 1 hour using a spatula at room temperature and 900 mmHg.

Step b): Crosslinking and Substitution

BDDE (30 mg, i.e. 0.15 mmol) and VSA (87 mg, i.e. 0.67 mmol) are added to the noncrosslinked sodium hyaluronate (NaHA) gel obtained in the preceding step, the combined mixture being homogenized using a spatula for approximately 30 minutes at a temperature of 12-14° C. The combined mixture is subsequently placed on a water bath at 50° C. for 2 h 10. The degree of crosslinking agent introduced DCI is equal to approximately 0.07 and the degree of substituent introduced DSI is equal to approximately 0.30.

STEP C): NEUTRALIZATION, PURIFICATION

The crosslinked and substituted final gel is subsequently neutralized by the addition of 1N HCl and placed in a phosphate buffer bath in order to stabilize the pH and to make possible the hydration or swelling thereof in order to obtain a gel comprising 20 mg/g of HA. This gel is subsequently homogenized before being packaged in syringes. A crosslinked and substituted NaHA hydrogel G5 is thus obtained.

Gel REF5 Synthesis

The gel REF5 is synthesized according to the procedure for the gel G5 described above, the VSA being replaced with water for parenteral injection (WPI).

Characterization of the elasticity of the gels G5 and REF5

The elasticity of the gels is characterized on a TA Instruments AR 2000 Ex rheometer described in example 2; the results are given in table VII below.

TABLE VII

|  | G5 | REF5 |
|---|---|---|
| Elasticity: G' (Pa) at 1 Hz | 519 | 433 |

The substitution makes it possible to obtain finished products having a higher elasticity. These rheological data, like those of example 2 (NaHA of high molecular weight), confirm that the substitution can be carried out on NaHA having different molecular weights.

Example 6

VSA (sodium salt of vinylsulfonic acid) substitution on CMC (carboxymethylcellulose) simultaneously with crosslinking by BDDE (1,4-butanediol diglycidyl ether), at a temperature of 50° C. and in an alkaline medium (RCR=1:1)

This example makes it possible to demonstrate by rheology the substitution on a polysaccharide other than NaHA.

Gel G6 Synthesis

Step a): Hydration of CMC in the Form of a Noncrosslinked Gel 0.93 g, i.e. 2.20 mmol of sodium CMC (supplied by Sigma, molecular weight: approximately 1.0 MDa) is weighed out in a container. A 1% aqueous solution of sodium hydroxide (0.25 mol/L, i.e. 2.25 mmol of HO⁻ introduced into the reaction medium) in water (9.0 g) is added (RCR=1:1) and the combined mixture is homogenized for approximately 90 minutes using a spatula at room temperature and 900 mmHg.

Step b): Crosslinking and Substitution

BDDE (37 mg, i.e. 0.18 mmol) and VSA (87 mg, i.e. 0.67 mmol) are added to the noncrosslinked CMC gel obtained in the preceding step, the combined mixture being homogenized using a spatula for approximately 30 minutes at a temperature of 12-14° C. The combined mixture is subsequently placed on a water bath at 50° C. for 3 h 35. The degree of crosslinking agent introduced DCI is equal to approximately 0.08 and the degree of substituent introduced DSI is equal to approximately 0.30.

Step c): Neutralization, Purification

The crosslinked and substituted final gel is subsequently neutralized by the addition of 1N HCl and placed in a phosphate buffer bath in order to stabilize the pH and to make possible the hydration or swelling thereof in order to obtain a gel comprising 30 mg/g of CMC. This gel is subsequently homogenized before being packaged in syringes. A crosslinked and substituted CMC hydrogel G6 is thus obtained.

Gel REF6 Synthesis

The gel REF6 is synthesized according to the procedure for the gel G6 described above, the VSA being replaced with water for parenteral injection (WPI).

Characterization of the elasticity of the gels G6 and REF6

The elasticity of the gels is characterized on a TA Instruments AR 2000 Ex rheometer described in example 2; the results are given in table VIII below.

TABLE VIII

|  | G6 | REF6 |
|---|---|---|
| Elasticity: G' (Pa) at 1 Hz | 524 | 483 |

The substitution makes it possible to obtain finished products having a higher elasticity. These rheological data, like those of example 2 (NaHA), confirm that the substitution can be carried out on different polysaccharide backbones, in particular cellulose derivatives.

Example 7

EB (epoxybutane) substitution on CH (chitosan) simultaneously with crosslinking by BDDE (1,4-butanediol diglycidyl ether), at a temperature of 50° C. and in a weak acidic medium (RCR=0.06:1) and strong acidic medium (RCR=1:1)

This example makes it possible to demonstrate by rheology the substitution in an acidic medium simultaneously with the crosslinking.

Gel G1A Synthesis (in a Weak Acidic Medium)

Step a): Hydration of CH in the Form of a Noncrosslinked Gel 0.99 g, i.e. 2.93 mmol, of CH with a degree of deacetylation of the order of 80% (supplied by Kitozyme, molecular weight: approximately 120 000 Da) is weighed out in a container. A 1% aqueous solution of glutamic acid (0.07 mol/L) in water (9.0 g) is added. As glutamic acid is a weak acid, it is partially dissociated in water. The pH of the aqueous solution can be calculated via the following formula (determined as a result of approximations): $pH=(\frac{1}{2} pKa)-(\frac{1}{2} \log [\text{Glutamic Acid}])$, i.e. $pH=(\frac{1}{2}\times2.19)\times(\frac{1}{2}\times\log(0.07))=1.67$. The concentration of hydronium $H_3O^+$ ion can be calculated by the following formula: $[H_3O^+]=10^{-pH}$, i.e. $[H_3O^+]=0.02$ mol/L, i.e. 0.19 mmol of hydronium ions introduced into the reaction medium (RCR=0.06:1). The combined mixture is homogenized for approximately 90 minutes using a spatula at room temperature and 900 mmHg. The pH of the reaction medium is 5.3.

Step b): Crosslinking and Substitution

BDDE (60 mg, i.e. 0.30 mmol) and EB (337 mg, i.e. 4.68 mmol) are added to the noncrosslinked CH gel obtained in the preceding step, the combined mixture being homogenized using a spatula for approximately 30 minutes at a temperature of 12-14° C. The combined mixture is subsequently placed on a water bath at 50° C. for. The degree of crosslinking agent introduced DCI is equal to approximately 0.10 and the degree of substituent introduced DSI is equal to approximately 1.60.

STEP C): NEUTRALIZATION, PURIFICATION

The crosslinked and substituted final gel is subsequently neutralized by the addition of 1N sodium hydroxide solution and placed in a phosphate buffer bath in order to stabilize the pH and to make possible the hydration or swelling thereof in order to obtain a gel comprising 22 mg/g of CH. This gel is subsequently homogenized before being packaged in syringes which are sterilized by autoclaving. A crosslinked, substituted and sterilized CH hydrogel G7a is thus obtained.

Gel G7b Synthesis (in a Strong Acidic Medium)

Step a): Hydration of CH in the Form of a Noncrosslinked Gel 0.99 g, i.e. 2.93 mmol, of CH with a degree of deacetylation of the order of 80% (supplied by Kitozyme, molecular weight: approximately 120 000 Da) is weighed out in a container. A 1.15% aqueous solution of hydrochloric acid (0.32 mol/L, i.e. 2.88 mol of $H_3O^+$ ions introduced into the reaction medium=>RCR=1:1) in water (9.0 g) is added. The combined mixture is homogenized for approximately 90 minutes using a spatula at room temperature and 900 mmHg. The pH of the reaction medium is 3.

Step b): Crosslinking and Substitution

BDDE (60 mg, i.e. 0.30 mmol) and EB (337 mg, i.e. 4.68 mmol) are added to the noncrosslinked CH gel obtained in the preceding step, the combined mixture being homogenized using a spatula for approximately 30 minutes at a temperature of 12-14° C. The combined mixture is subsequently placed on a water bath at 50° C. for. The degree of crosslinking agent introduced DCI is equal to approximately 0.10 and the degree of substituent introduced DSI is equal to approximately 1.60.

Step c): Neutralization, Purification

The crosslinked and substituted final gel is subsequently neutralized by the addition of 1N sodium hydroxide solution and placed in a phosphate buffer bath in order to stabilize the pH and to make possible the hydration or swelling thereof in order to obtain a gel comprising 22 mg/g of CH. This gel is subsequently homogenized before being packaged in syringes which are sterilized by autoclaving. A crosslinked, substituted and sterilized CH hydrogel G7b is thus obtained.

Gel REF7 Synthesis

The gel REF7 is synthesized according to the procedure for the gel G7 described above, the EB being replaced with water for parenteral injection (WPI).

Characterization of the viscosity of the gels G7a and REF7

The 2 gels G7a and REF7 are more viscous than elastic in consistency and are thus characterized in viscosity.
The viscosity of the sterile gels is characterized on a TA Instruments AR 2000 Ex rheometer described in example 1; the results are given in table IX below.

TABLE IX

|  | G7a | REF7 |
|---|---|---|
| Viscosity (Pa · s) | 67.1 | 35.4 |

The substitution makes it possible to obtain finished products of greater rheology. These rheological data, like those of example 2 (NaHA under basic conditions) and 6 (CMC under basic conditions), confirm that the substitution can be carried out on different polysaccharide backbones and under both acidic and basic conditions.

Example 8

VSA (Sodium Salt of Vinylsulfonic Acid) Substitution on NaHA Simultaneously with Crosslinking by DVS (Divinyl Sulfone), at a Temperature of 40° C. and in an Alkaline Medium (RCR=1.75:1)

This example makes it possible to demonstrate by rheology the substitution on an NaHA bridged with different crosslinking agents.

Gel G8 Synthesis

Step a): Hydration of Sodium Hyaluronate Fibers in the Form of a Noncrosslinked Gel Sodium hyaluronate fibers of injectable grade (0.9 g, i.e. 2.24 mmol; molecular weight: approximately 2.7 MDa) are weighed out in a container. A 1% aqueous solution of sodium hydroxide (0.25 mol/L, i.e. 3.92 mmol of $HO^-$ introduced into the medium) in water (15.7 g) is added (RCR=1.75:1) and the combined mixture is homogenized for approximately 1 hour using a spatula at room temperature and 900 mmHg.

Step b): Crosslinking and Substitution

DVS (57 mg, i.e. 0.48 mmol) and VSA (87 mg, i.e. 0.67 mmol) are added to the noncrosslinked sodium hyaluronate (NaHA) gel obtained in the preceding step, the combined mixture being homogenized using a spatula for approximately 30 minutes at a temperature of 12-14° C. The combined mixture is subsequently placed on a water bath at 40° C. for 1 h 00. The degree of crosslinking agent introduced DCI is equal to approximately 0.21 and the degree of substituent introduced DSI is equal to approximately 0.30.

Step c): Neutralization, Purification

The crosslinked and substituted final gel is subsequently neutralized by the addition of 1N HCl and placed in a phosphate buffer bath in order to stabilize the pH and to make possible the hydration or swelling thereof in order to obtain a gel comprising 20 mg/g of HA. This gel is subsequently homogenized before being packaged in syringes. A crosslinked and substituted NaHA hydrogel G8 is thus obtained.

Gel REF8 Synthesis

The gel REF8 is synthesized according to the procedure for the gel G8 described above, the VSA being replaced with water for parenteral injection (WPI).

Characterization of the Elasticity of the Gels G8 and REF8

The elasticity of the gels is characterized on a TA Instruments AR 2000 Ex rheometer described in example 2; the results are given in table X below.

TABLE X

|  | G8 | REF8 |
|---|---|---|
| Elasticity: G' (Pa) at 1 Hz | 110 | 103 |

The substitution makes it possible to obtain finished products having a higher elasticity. These rheological data, like those of example 2 (crosslinking with BDDE), confirm that the substitution can be carried out at the same time as a bridging of the polysaccharide, whatever the nature of the crosslinking agent.

Example 9

SAS (Sodium Allyl Sulfate) Substitution on NaHA Simultaneously with Crosslinking by BDDE (1,4-Butanediol Diglycidyl Ether), at a Temperature of 50° C. and in an Alkaline Medium (RCR=0.8:1)

This example makes it possible to demonstrate, by rheology:
the substitution of the allyl functional group on the NaHA during crosslinking and the difference in structure introduced by the substitution,
the better resistance to radical decomposition of the gel substituted with a sulfate pendant group.

Gel G9 Synthesis

Step a): Identical to Step a) of the Synthesis of the Gel G1A

Step b): Crosslinking and Substitution

BDDE (65 mg, i.e. 0.32 mmol) and SAS (111 mg, i.e. 0.68 mmol) are added to the noncrosslinked sodium hyaluronate (NaHA) gel obtained in the preceding step, the combined mixture being homogenized using a spatula for approximately 30 minutes at a temperature of 12-14° C. The combined mixture is subsequently placed on a water bath at 50° C. for 2 h 10. The degree of crosslinking agent introduced DCI is equal to approximately 0.14 and the degree of substituent introduced DSI is equal to approximately 0.30.

Step c): Neutralization, Purification

The crosslinked and substituted final gel is subsequently neutralized by the addition of 1N HCl and placed in a phosphate buffer bath in order to stabilize the pH and to make possible the hydration or swelling thereof in order to obtain a gel comprising 20 mg/g of HA. This gel is subsequently homogenized before being packaged in syringes which are sterilized by autoclaving. A crosslinked, substituted and sterilized NaHA hydrogel G9 is thus obtained.

Gel REF9 Synthesis

The gel REF9 is synthesized according to the procedure of the gel G9 described above, the SAS being replaced with water for parenteral injection (WPI).

Characterization of the Elasticity of the Gels G9 and REF9

The elasticity of the sterile gels is characterized on a TA Instruments AR 2000 Ex rheometer described in example 2; the results are given in table XI below.

TABLE XI

|  | G9 | REF9 |
|---|---|---|
| Elasticity: G' (Pa) at 1 Hz | 123 | 105 |

The substitution makes it possible to obtain finished products of greater rheology (+17%). These rheological data confirm the substitution of the allyl functional group on the NaHA simultaneously with the crosslinking.

Test on Radical Decomposition of the Gels G9 and REF9

The gels were also characterized by a test on in vitro radical decomposition at the temperature, described in example 2. The half-lives obtained are given in table XII below.

TABLE XII

|  | G9 | REF9 |
|---|---|---|
| Half-life (minutes) | 12.6 | 6.6 |

Thus, the half-lives of the gels substituted with a sulfate pendant group obtained according to the invention are longer, guaranteeing a greater time of persistence in vivo.

Counterexamples

Counterexample 1

This counterexample is similar to example 1 carried out under drastic temperature and pH conditions of the prior art.

a) Gel G1Ca Synthesis: Substitution of VSA (Sodium Salt of Vinylsulfonic Acid) on NaHA Simultaneously with Crosslinking by BDDE (1,4-Butanediol Diglycidyl Ether), at a Temperature of 80° C. And in a Concentrated Alkaline Medium (RCR of 4.1:1)

Step a): Hydration of Sodium Hyaluronate Fibers in the Form of a Noncrosslinked Gel Sodium hyaluronate fibers of injectable grade (0.9 g, i.e. 2.24 mmol; molecular weight: approximately 2.7 MDa) are weighed out in a container. A 5% aqueous solution of sodium hydroxide (1.25 mol/L, i.e. 9.25 mmol of HO⁻ introduced into the medium) in water (7.4 g) is added (RCR of 4.1:1) and the combined mixture is homogenized for approximately 1 hour using a spatula at room temperature and 900 mmHg.

Step b): Crosslinking and Substitution

BDDE (65 mg, i.e. 0.32 mmol) and VSA (102 mg, i.e. 0.78 mmol) are added to the noncrosslinked sodium hyaluronate (NaHA) gel obtained in the preceding step, the combined mixture being homogenized using a spatula for approximately 30 minutes at a temperature of 12-14° C. The combined mixture is subsequently placed on a water bath at 80° C. for 2 h 10 in order to obtain a degree of crosslinking agent introduced DCI of approximately 0.14 and a degree of substituent introduced DSI of approximately 0.35.

After 20 minutes at 80° C., the reaction medium has completely decomposed (liquid, brown, "caramelized" appearance).

A high temperature (80° C.) and the use of a concentrated sodium hydroxide solution decompose the polysaccharide network and thus disrupt the substitution and the crosslinking of the polymer chains.

b) Gel G1Cb synthesis: Substitution of VSA (sodium salt of vinylsulfonic acid) on NaHA simultaneously with crosslinking by BDDE (1,4-butanediol diglycidyl ether), at a temperature of 80° C. and in a concentrated alkaline medium (RCR of 8.2:1)

Step a): Hydration of Sodium Hyaluronate Fibers in the Form of a Noncrosslinked Gel Sodium hyaluronate fibers of injectable grade (0.9 g, i.e. 2.24 mmol; molecular weight: approximately 2.7 MDa) are weighed out in a container. A 10% aqueous solution of sodium hydroxide (2.5 mol/L, i.e. 18.5 mmol of HO⁻ introduced into the medium) in water (7.4 g) is added (RCR of 8.2:1) and the combined mixture is homogenized for approximately 1 hour using a spatula at room temperature and 900 mmHg.

Step b): Crosslinking and Substitution

BDDE (65 mg, i.e. 0.32 mmol) and VSA (102 mg, i.e. 0.78 mmol) are added to the noncrosslinked sodium hyaluronate (NaHA) gel obtained in the preceding step, the combined mixture being homogenized using a spatula for approximately 30 minutes at a temperature of 12-14° C. The combined mixture is subsequently placed on a water bath at 80° C. for 2 h 10 in order to obtain a degree of crosslinking agent introduced DCI of approximately 0.14 and a degree of substituent introduced DSI of approximately 0.35.

After 15 minutes at 80° C., the reaction medium has completely decomposed (liquid, brown, "caramelized" appearance).

A high temperature (80° C.) and the use of a concentrated sodium hydroxide solution decompose the polysaccharide network and thus disrupt the substitution and the crosslinking of the polymer chains.

Counterexample 2

This counterexample is similar to example 6 carried out under drastic temperature and pH conditions of the prior art.

a) VSA (sodium salt of vinylsulfonic acid) substitution on CMC (carboxymethylcellulose) simultaneously with crosslinking by BDDE (1,4-butanediol diglycidyl ether), at a temperature of 80° C. and in a concentrated alkaline medium (RCR of 5.1:1)

Gel G6a Synthesis

Step a): Hydration of CMC in the Form of a Noncrosslinked Gel 0.93 g, i.e. 2.20 mmol of sodium CMC (supplied by Sigma, molecular weight: approximately 1.0 MDa) is weighed out in a container. A 5% aqueous solution of sodium hydroxide (1.25 mol/L, i.e. 11.25 mmol of HO⁻ introduced into the medium) in water (9.0 g) is added (RCR of 5.1:1) and the combined mixture is homogenized for approximately 90 minutes using a spatula at room temperature and 900 mmHg.

Step b): Crosslinking and Substitution

BDDE (37 mg, i.e. 0.18 mmol) and VSA (87 mg, i.e. 0.67 mmol) are added to the noncrosslinked CMC gel obtained in the preceding step, the combined mixture being homogenized using a spatula for approximately 30 minutes at a temperature of 12-14° C. The combined mixture is subsequently placed on a water bath at 80° C. for 3 h 35 in order to obtain a degree of crosslinking agent introduced DCI of approximately 0.08 and a degree of substituent introduced DSI of approximately 0.30.

Step c): Neutralization, Purification

The crosslinked and substituted final gel is subsequently neutralized by the addition of 1N HCl and placed in a phosphate buffer bath in order to stabilize the pH and to make possible the hydration or swelling thereof in order to obtain a gel comprising 30 mg/g of CMC. This gel is subsequently homogenized before being packaged in syringes. A crosslinked and substituted CMC hydrogel G6a is thus obtained.

The gel has an excessively liquid, excessively dispersive and not sufficiently elastic appearance.

b) VSA (sodium salt of vinylsulfonic acid) substitution on CMC (carboxymethylcellulose) simultaneously with crosslinking by BDDE (1,4-butanediol diglycidyl ether), at a temperature of 80° C. and in a concentrated alkaline medium (RCR of 10.2:1)

Gel G6b Synthesis

Step a): Hydration of CMC in the Form of a Noncrosslinked Gel 0.93 g, i.e. 2.20 mmol of sodium CMC (supplied by Sigma, molecular weight: approximately 1.0 MDa) is weighed out in a container. A 10% aqueous solution of sodium hydroxide (2.5 mol/L, i.e. 22.5 mmol of HO⁻ introduced into the medium) in water (9.0 g) is added (RCR of 10.2:1) and the combined mixture is homogenized for approximately 90 minutes using a spatula at room temperature and 900 mmHg.

Step b): Crosslinking and Substitution

BDDE (37 mg, i.e. 0.18 mmol) and VSA (87 mg, i.e. 0.67 mmol) are added to the noncrosslinked CMC gel obtained in the preceding step, the combined mixture being homogenized using a spatula for approximately 30 minutes at a temperature of 12-14° C. The combined mixture is subsequently placed on a water bath at 80° C. for 3 h 35 in order to obtain a degree of crosslinking agent introduced DCI of approximately 0.08 and a degree of substituent introduced DSI of approximately 0.30.

Step c): Neutralization, Purification

The crosslinked and substituted final gel is subsequently neutralized by the addition of 1N HCl and placed in a phosphate buffer bath in order to stabilize the pH and to make possible the hydration or swelling thereof in order to obtain a gel comprising 30 mg/g of CMC. This gel is subsequently homogenized before being packaged in syringes. A crosslinked and substituted CMC hydrogel G6b is thus obtained.

The gel has an excessively liquid, excessively dispersive and not sufficiently elastic appearance.

c) Characterization of the Elasticity of the Gels G6a and G6b

The elasticity of the gels is characterized on a TA Instruments AR 2000 Ex rheometer described in example 2; the results are given in the table below.

|  | G6a | G6b | G6 | REF6 |
|---|---|---|---|---|
| Elasticity: G' (Pa) at 1 Hz | 17 | 12 | 524 | 483 |

The rheological data confirm the aspects observed: the gels do not have the expected consistency and they do not exhibit the viscoelastic properties required for the applications targeted.

A high temperature (80° C.) and the use of a concentrated sodium hydroxide solution decompose the polysaccharide network and thus disrupt the grafting and the crosslinking of the polymer chains.

The invention claimed is:

1. A process for obtaining a substituted and crosslinked polysaccharide, comprising:
    performing simultaneous substitution and crosslinking of a polysaccharide in an aqueous reaction medium by reacting at least one precursor of a substituent and a crosslinking agent with hydroxyl functional groups of the polysaccharide, in the presence of a basic or acidic catalyst at a concentration between $3.16 \times 10^{-7}$ and 0.32 mol/L, and at a temperature of less than 60° C.; and
    obtaining the substituted and crosslinked polysaccharide in gel form after the simultaneous substitution and crosslinking of the polysaccharide is performed,
    wherein:
    the polysaccharide is chosen from the group consisting of hyaluronic acid and salts thereof, chitosan, cellulose, and derivatives thereof;
    the crosslinking agent is chosen from the group consisting of ethylene glycol diglycidyl ether, butanediol diglycidyl ether, polyglycerol polyglycidyl ether, polyethylene glycol diglycidyl ether, polypropylene glycol diglycidyl ether, a bisepoxy or a polyepoxy, a dialkyl sulfone, divinyl sulfone, formaldehyde, and glutaraldehyde;
    the precursor of the substituent comprises a single reactive functional group capable of forming a bond with a hydroxyl functional group of the polysaccharide, the reactive functional group being chosen from the group consisting of substituted or unsubstituted vinyl, substituted or unsubstituted epoxide, substituted or unsubstituted allyl, ketone, aldehyde, thiocyanate, halide, isocyanate, halosilicon, nitrile and sultone functional groups; and
    substitution is not carried out via the crosslinking agent.

2. The process as claimed in claim 1, wherein a reactive catalyst ratio (RCR), defined as being:

$$RCR = \frac{\text{(Number of moles reactive functional groups of the catalyst introduced into the reaction medium)}}{\text{(Number of moles } disacharide \text{ unit introduced into the reaction medium)}},$$

is between 0.02:1 and 3:1.

3. The process as claimed in claim 2, wherein the reactive catalyst ratio (RCR) is between 0.2:1 and 3:1.

4. The process as claimed in claim 1, wherein the catalyst is a base.

5. The process as claimed in claim 4, wherein the base is an inorganic base and is sodium hydroxide or potassium hydroxide and wherein the reactive functional group of the catalyst is the OH$^-$ ion.

6. The process as claimed in claim 5, wherein the concentration by weight of the inorganic base is between $1.2 \times 10^{-5}$% and 1.15%.

7. The process as claimed in claim 4, wherein the reactive functional group of the catalyst is the HO$^-$ ion at a concentration between $10^{-6}$ mol/L and 0.32 mol/L, such that $10^{-6}$ mol/L ≤ [HO$^-$] ≤ 0.32 mol/L.

8. The process as claimed in claim 4, wherein the pH of the aqueous reaction medium is basic and is between 8.5 and 13.5.

9. The process as claimed in claim 1, wherein the catalyst is an acid.

10. The process as claimed in claim 9, wherein the acid is an inorganic acid and is hydrochloric acid and the reactive functional group of the catalyst is the H$_3$O$^+$ ion.

11. The process as claimed in claim 10, wherein the concentration by weight of the inorganic acid is between $1.14 \times 10^{-5}$% and 1.3%.

12. The process as claimed in claim 9, wherein the acid is an organic acid chosen from the group consisting of glutamic acid and acetic acid.

13. The process as claimed in claim 12, wherein the concentration by weight of the organic acid is between 0.25% and 2%.

14. The process as claimed in claim 9, wherein the reactive functional group of the catalyst is the H$_3$O$^+$ ion at a concentration between $3.16 \times 10^{-7}$ mol/L and 0.01 mol/L, such that $3.16 \times 10^{-7}$ mol/L ≤ [H$_3$O$^+$] ≤ 0.01 mol/L.

15. The process as claimed in claim 9, wherein the pH of the aqueous reaction medium is acidic and is between 2 and 6.5.

16. The process as claimed in claim 1, wherein the molecular weight Mw of the polysaccharide is within a range from 0.01 MDa to 4.0 MDa.

17. The process as claimed in claim 1, wherein the precursor of the substituent further comprises at least one group or functional group chosen from the group consisting of sulfonate, linear or branched alkyl, substituted or unsubstituted aromatic, sulfate, thiol, monosaccharide, phosphate, phosphonate, carbonate and ester groups and functional groups.

18. The process as claimed in claim 1, wherein the precursor of the substituent is chosen from the group consisting of allyl-sulfates, vinyl-sulfonates, epoxy-sulfates and epoxy-alkanes.

19. The process as claimed in claim 1, wherein the precursor of the substituent is chosen from the group consisting of vinylsulfonic acid and salts thereof, epoxybutane and sodium allyl sulfate.

20. The process as claimed in claim 1, wherein the substituted and crosslinked polysaccharide has a degree of substituent introduced (DSI), defined as being:

$$DSI = \frac{\text{(Number of moles of reactive \emph{fonctional} groups of the substituent introduced into the reaction medium)}}{\text{(Number of moles of \emph{disaccharide} unit introduced into the reaction medium)}},$$

within a range from 0.001 to 4.00.

21. The process as claimed in claim 1, wherein the substituted and crosslinked polysaccharide has a degree of crosslinking agent introduced (DCI), defined as being:

$$DCI = \frac{\text{(Number of moles crosslinking agent introduced into the reaction medium)}}{\text{(Number of moles \emph{disacharide} unit introduced into the reaction medium)}},$$

within a range from 0.001 to 0.5.

22. The process as claimed in claim 1, wherein the temperature is between 39° C. and 60° C.

23. The process as claimed in claim 1, wherein the simultaneous substitution and crosslinking reaction is performed for a time period from 15 minutes to 48 hours.

24. The process as claimed in claim 1, further comprising washing the substituted and crosslinked polysaccharide.

25. The process as claimed in claim 1, further comprising:
neutralizing the gel formed from the substituted and crosslinked polysaccharide; and
hydrating the neutralized gel with an aqueous medium,
wherein neutralization and hydration are performed to formulate the gel for use as a viscosupplementation composition.

26. The process as claimed in claim 1, further comprising:
neutralizing the gel formed from the substituted and crosslinked polysaccharide; and
hydrating the neutralized gel with an aqueous medium,
wherein neutralization and hydration are performed to formulate the gel for use as a composition for filling in wrinkles.

27. The process as claimed in claim 1, wherein the polysaccharide is hyaluronic acid or sodium hyaluronate, the crosslinking agent is 1,4-butanediol diglycidyl ether, and the precursor of the substituent is sodium vinylsulfonate.

28. The process as claimed in claim 1, wherein the polysaccharide is hyaluronic acid or sodium hyaluronate, the crosslinking agent is 1,4-butanediol diglycidyl ether, and the precursor of the substituent is epoxybutane.

29. The process as claimed in claim 1, wherein the polysaccharide is hyaluronic acid or sodium hyaluronate, the crosslinking agent is 1,4-butanediol diglycidyl ether, and the precursor of the substituent is sodium allyl sulfate.

30. The process as claimed in claim 1, wherein the polysaccharide is hyaluronic acid or sodium hyaluronate, the crosslinking agent is divinyl sulfone, and the precursor of the substituent is sodium vinylsulfonate.

* * * * *